United States Patent
Suki et al.

(10) Patent No.: US 6,907,881 B2
(45) Date of Patent: Jun. 21, 2005

(54) VARIABLE PEAK PRESSURE VENTILATION METHOD AND SYSTEM

(75) Inventors: Bela Suki, Newton, MA (US); Kenneth R. Lutchen, Framingham, MA (US); Edward P. Ingenito, Kingston, MA (US)

(73) Assignees: The Trustees of Boston University, Boston, MA (US); Brigham and Women's Hospital, Boston, MA (US)

(*) Notice: Subject to any disclaimer, the term of this patent is extended or adjusted under 35 U.S.C. 154(b) by 0 days.

(21) Appl. No.: 10/123,059

(22) Filed: Apr. 12, 2002

(65) Prior Publication Data

US 2003/0029452 A1 Feb. 13, 2003

Related U.S. Application Data

(63) Continuation of application No. PCT/US00/26255, filed on Oct. 13, 2000.
(60) Provisional application No. 60/159,386, filed on Oct. 14, 1999.

(51) Int. Cl.[7] .............................................. A61M 16/00
(52) U.S. Cl. .............................. 128/204.21; 128/204.23
(58) Field of Search ....................... 128/204.28, 204.21, 128/204.23, 204.26

(56) References Cited

U.S. PATENT DOCUMENTS

| | | | | |
|---|---|---|---|---|
| 4,957,107 A | * | 9/1990 | Sipin ..................... | 128/204.21 |
| 5,245,995 A | | 9/1993 | Sullivan et al. | |
| 5,316,009 A | | 5/1994 | Yamada | |
| 5,582,182 A | * | 12/1996 | Hillsman ................... | 600/532 |
| 5,692,497 A | | 12/1997 | Schnitzer et al. | |
| 5,704,345 A | | 1/1998 | Berthon-Jones | |
| 6,029,665 A | * | 2/2000 | Berthon-Jones ........ | 128/204.23 |
| 6,138,675 A | * | 10/2000 | Berthon-Jones ........ | 128/204.23 |
| 6,484,719 B1 | * | 11/2002 | Berthon-Jones ........ | 128/204.23 |
| 6,575,163 B1 | * | 6/2003 | Berthon-Jones ........ | 128/204.18 |

\* cited by examiner

*Primary Examiner*—Aaron J. Lewis
(74) *Attorney, Agent, or Firm*—Nixon Peabody LLP

(57) ABSTRACT

A system and method for ventilating a lung in a living being by varying the peak inspiratory pressure. The peak inspiratory pressure may deviate about a mean that is chosen to correspond with a knee in a pressure-volume curve of the lung.

24 Claims, 5 Drawing Sheets

VARIABLE PEAK PRESSURE VENTILATION METHOD AND SYSTEM

This application is a continuation of copending application PCT/US00/26255, filed Oct. 13, 2000, incorporated herein by reference, which claims benefit of provisional application 60/159,386, filed Oct. 14, 1999.

This invention was made with Government Support under Contract Number BES-9813599 awarded by the National Science Foundation. The Government has certain rights in the invention.

BACKGROUND OF THE INVENTION

1. Field of the Invention

The present invention relates to the field of life support systems. In particular, the present invention relates to the field of ventilation systems and methods.

2. Description of the Related Art

For over forty years, mechanical ventilators have been one of the most important life-support systems for the treatment of respiratory failure. These mechanical ventilators have been designed to provide a predetermined volume of air for each breath. The volume of air being based upon a patient's weight and sometimes height. Although it is known that following a long period of mechanical ventilation in certain types of pre-existing lung disease some form of mechanical damage to the lungs can develop, the basic protocols of mechanical ventilation have not significantly changed. Many experimental studies have reported that patients with acute lung injury associated with acute respiratory distress syndrome (ARDS) are particularly at risk of ventilator-induced lung injury and subsequent worsening of their condition.

A significant problem in acute respiratory distress syndrome is that at the end of an expiration alveolar regions collapse with a concomitant impairment in gas exchange. To recruit these collapsed regions, ventilation is usually superimposed on a positive end-expiratory pressure (PEEP). Superimposing breaths on top of PEEP to improve gas exchange unfortunately has adverse effects on lung stretching, and tends to cause high peak airway pressures. The lung tissue then becomes over-distended. As a consequence, micro-vascular permeability increases due to endothelial cell damage which, in turn, causes alveolar and peribronchial edema and, perhaps in later stages, protein influx into the alveolar gas exchange region hindering oxygen uptake. To avoid these problems, the use of a combination of positive end-expiratory pressure sufficient to keep most airways open and low tidal volume to reduce distention at the end of each breath ventilation has been suggested to improve oxygenation at the expense of some deterioration in carbon dioxide elimination. However, several problems arise. First, because of CO2 accumulation, respiratory acidosis may develop leading to serious clinical complications. Second, if the positive end-expiratory pressure is not sufficiently high, regions in the periphery of the lung will still be prone to collapse toward end-expiration. During ventilation, these regions may repeatedly undergo opening and closing and hence extreme high shear stresses can develop along the airway walls. Thus, if the same region repeatedly collapses and reopens many times, the non-physiological shear forces will eventually lead to damaging the epithelial cell layer causing protein influx into the alveoli and stress-induced cytokine expression. This initiates a self propagating state of mechanically activated inflammation. Third, while low tidal volume ventilation reduces mortality in ARDS, it does not eliminate it.

Thus, a delicate balance of positive end-expiratory pressure and tidal volume is needed to achieve the least injurious ventilation protocol and the best blood gas levels and this balance has to be continuously monitored and updated. Furthermore, in certain instances, some regions of lung will experience optimal conditions of ventilation in which shear stress is minimized, while adjacent more severely injured regions will experience ventilator-induced injury. Due to these difficulties, there has been little consensus on what strategy would be optimal in reducing the risk of ventilator-induced lung injury.

In 1996 Lefevre et al. introduced "biologic variability" into mechanical ventilation as a potential alternative to conventional mechanical ventilation (G. R. Lefevre, J. E. Kowalski, L. G. Girling, O. B. Thiessen, and W. A. C. Mutch, *Am. J. Respir. Crit. Care Med.*, 154, 1567–1572 (1996)). Lefevre et al. pointed out that while spontaneous variability of all physiologic rhythms are essential features of living organisms, conventional life-support systems eliminate this inherent variability. They introduced a computer-controlled ventilator such that the tidal volume was taken from a Gaussian distribution and the respiratory rate was adjusted to keep minute ventilation constant. They found that, in a pig model of oleic acid induced lung injury, arterial blood gases improved significantly using this computer-controlled ventilation mode compared to conventional ventilation. Lefevre et al. termed their ventilation mode "biologic variability" because their frequencies mimic the variability of natural breathing frequency.

Nevertheless, Lefevre et al did not offer any mechanistic explanation for their findings. In two subsequent studies, Mutch and colleagues expanded their work to show that this ventilation mode works over longer ventilation periods and using positive end-expiratory pressure.

SUMMARY OF THE INVENTION

The inventors developed the present invention using a simple computer model of lung injury and provided an explanation for the findings in the experimental study of Lefevre, et al. The model is based upon observations of lungs which have been mechanically ventilated for a long period of time. Such a lung is likely to have a significant number of airways that are closed. Substantial collapsed areas in the lung are reflected in a reduced respiratory compliance which characterizes the ability of the lung tissue to take up air volume during inspiration. The inventors observed that there is no or very little volume change in a lung until a critical threshold pressure is exceeded. Once the critical threshold pressure is exceeded a rapid, avalanche-like volume change takes place. The inventor's model simulates this behavior by incorporating this concept that airways open in avalanches in an anatomically based tree model. The inventors have observed that an airway will pop open almost instantaneously when the inflation pressure exceeds a threshold pressure. During inspiration, when an airway pops open, all airways downstream will also open if their critical pressure is less than the inflation pressure. These newly opened airways can significantly contribute to the pressure-volume behavior of a lung.

The inventors discovered how variability in ventilation pressure can result in improved blood oxygenation. The inventors developed the present invention which is based on a variability that is added to peak inspiratory pressure, rather than tidal volume as in the Lefevre study. This simple modification results in a significant improvement in ventilator performance compared to the Lefevre et al. approach.

The inventor's mode of ventilation provides a variability in peak airway pressure such that the end-inspiratory pressure value is varied from inflation to inflation. While the inventors have learned that a peak end inspiratory pressure may have less volume than a standard end inspiratory pressure, the inventors have discovered that the gain in volume provided by an equal increase in pressure above the standard end inspiratory pressure provides a much larger gain in volume than what may have been lost to a lower pressure inspiration when averaged over several breaths. After a sufficient number of cycles, the inventors have discovered that the average recruited volume is much larger than with a conventional ventilation with a fixed peak end inspiratory pressure. The inventors discovered that the increase in recruited lung volume may be as large as 200% or more. As a consequence, the surface area available for gas exchange also increases which, in turn, results in a much improved blood oxygenation.

The present invention may lead to a substantial improvement in gas exchange without a concomitant decrease in mean airway pressure. The present invention may also present far fewer alveolar regions from becoming atelectactic or collapsed. Additionally, the present invention obviates the need for the peak end expiratory pressure mode of ventilation and, therefore, may avoid high airway pressures that have been shown to cause direct mechanical failure of pulmonary microvasculature, that can result in capillary injury and microvascular leakage, platelet activation and degranulation and neutrophil adhesion and influx.

The present invention may also prevent high shear forces on the alveolar compartment and lower the level of inflammatory cytokines including TNFalpha, IL-1B, IL-6, IL-8, and IL-12 within the alveolar compartment which can locally propagate the inflammatory response by causing further neutrophil influx and activation. Thus, the present invention may not only improve gas exchange, but may also minimize injury propagation in the tissue and have a significant impact on both morbidity and mortality in acute lung injury.

BRIEF DESCRIPTION OF THE DRAWINGS

The predetermined embodiments of this invention will be described in detail, with reference to the following figures.

DETAILED DESCRIPTION OF THE PREFERRED EMBODIMENTS

The present invention involves controlling the pressure of air being delivered by a ventilator such that the peak pressure varies from cycle to cycle. Since standard conventional and presently available mechanical ventilators only deliver gas by controlling the volume of gas, the inventors developed a method and system to control these conventional ventilators to deliver varying peak pressure to a patient.

Figure 1:
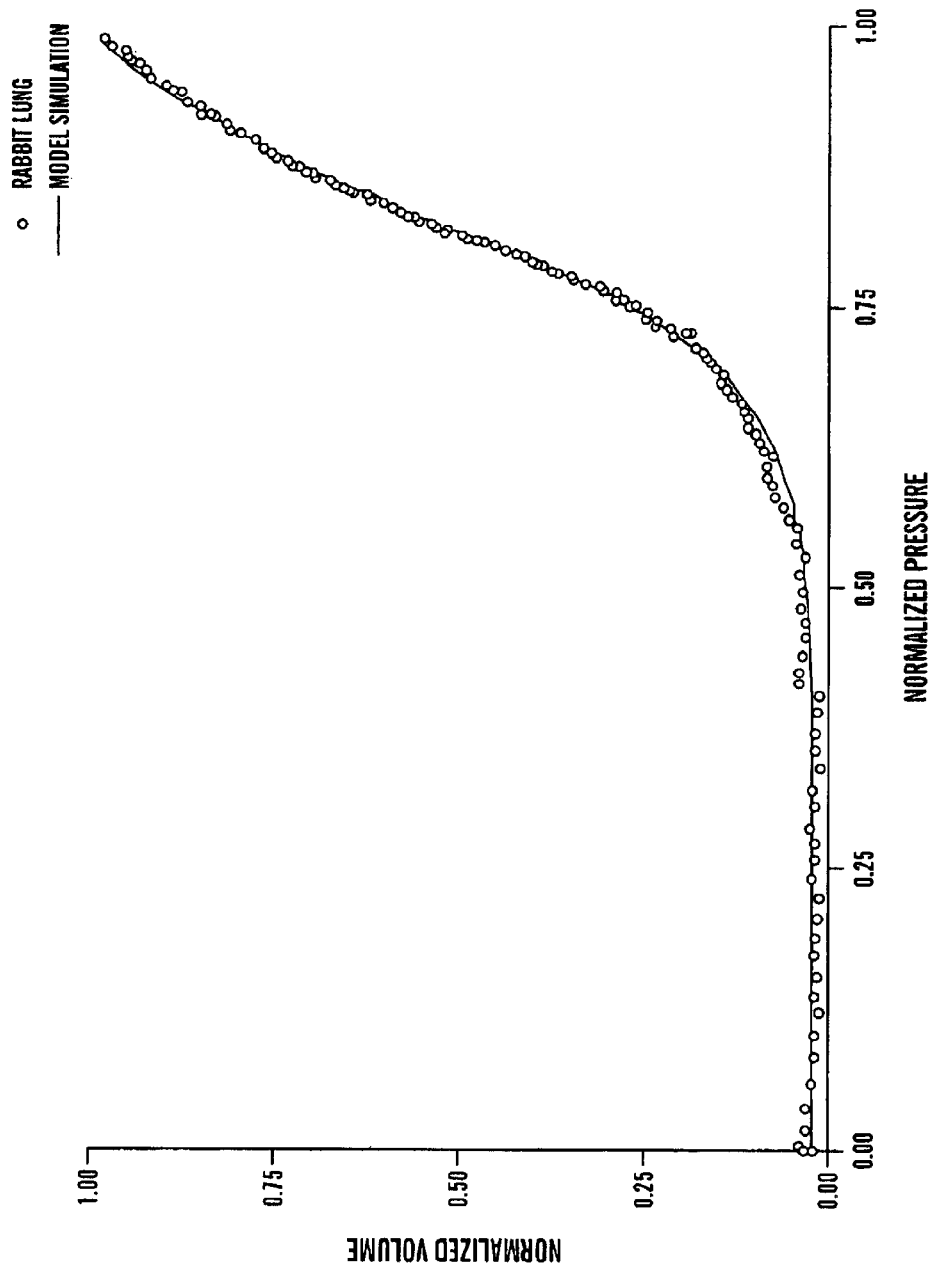
FIG. 1 is a graph of the normalized pressure-volume characteristics of a rabbit lung superimposed upon a model of the rabbit lung.

The inventors observed the pressure-volume curve of a typical injured lung. FIG. 1 shows a graph of a normalized inspiratory pressure-volume curve for a degassed rabbit lung. Degassing the lung leads to collapse and mimics acute respiratory distress syndrome (ARDS) The inventors noted that no volume change takes place until pressure increase above 0.7. However, around 0.75, a rapid, avalanche-like volume increase takes place. Experimental data obtained by the inventors have shown that an airway will pop open almost instantaneously when the external inflation pressure reaches a critical opening pressure. During inspiration, when an airway pops open, all airways below this segment will also open if the critical opening pressure is less than the external inflation pressure. This defines an avalanche whereby many airways open simultaneously connecting a given alveolar airspace to the trachea. The recruitment of alveoli by these avalanches can significantly contribute to the pressure-volume behavior of a lung.

In a symmetric tree structure, the inventors have arrived at the following equation which provides one method of relating the volume of air being delivered by a given pressure:

$$V = P^n \quad (1)$$

Where:
V is the normalized volume of air;
P is the normalized pressure of the air; and
n is the approximate number of generations of collapsed airways.

The more seriously injured the lung, the higher the value of n. We can, therefore, simulate a desired pressure-volume curve with a given n, generate a uniform random distribution of peak airway pressures around the knee of the pressure-volume curve and calculate a corresponding sequence of tidal volumes. While the inventors realize that this equation may not provide an exact model for the pressure-volume characteristics of a lung, it is a reasonably accurate representation of observed physiology, and currently there is no better model available. However, it is understood that further development of the present invention may provide other models upon which to apply the present invention.

Figure 2:
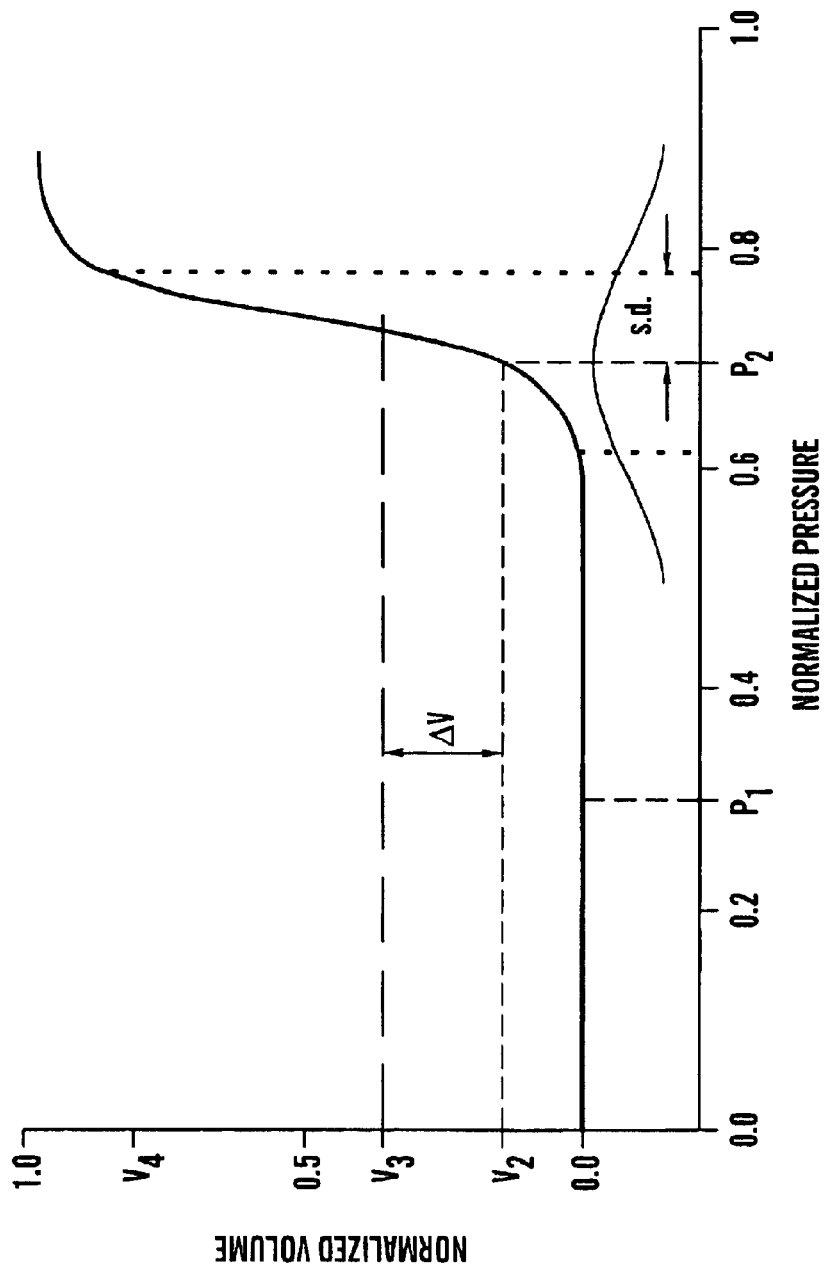
FIG. 2 is a graph of a normalized pressure-volume characteristic curve of a lung of a living being with superimposed peak inspiratory pressure variation.

The inventors have used this model to simulate the process of ventilation in a damaged lung which is partially collapsed and modified it to apply one embodiment of the present invention. The inventors added elasticity to the pressure-volume model to account for the already open alveoli to further expand when pressure is increased. This mechanism causes a plateau in volume at high pressure as shown in FIG. 2. In a lung experiencing acute respiratory distress syndrome, a large portion of the lung behaves according to the pressure-volume curve shown in FIG. 2. With conventional mechanical ventilation, the external inflation pressure increases every breath from the end-expiratory pressure, P1, to a constant value, P2. The corresponding recruited volume is V2 as shown in FIG. 2. When an embodiment of the present invention is applied to the same lung such that the end inspiratory value of the external inflation pressure is varied around P2 from inflation to inflation, the recruited volume increases substantially. For example, in one inflation the external inflation pressure increases to only 0.6 where recruited volume is lost. Then, in the next inflation the external inflation pressure increases to 0.8 which gains a significant amount of recruited volume and arrives at a volume of V4. Thus, due to the highly steep slope of the pressure-volume curve about P2, the gain in recruited volume is far greater than the loss in volume. In other words, the avalanche phenomenon yields a significantly larger ventilated volume for these two consecutive breaths. Thus, after a sufficient number of cycles, the average recruited volume becomes much larger compared to the case of conventional ventilation with a fixed end-inspiratory pressure. Results obtained by the inventors have shown an increase in volume of more than 200%. Additionally, as a result of this additional recruited volume, the surface area for gas exchange is also much larger which in turn results in an improved blood oxygenation.

An example of the application of one embodiment of the present invention follows: Six Hartley Guinea pigs (wt 400–800 g) were anesthetized with intraperitoneal xylazine (5–10 ml/kg) and pentobarbital (40 mg/kg). The animals were then tracheotomized and a carotid arterial line was placed for blood gas measurements. In order to assess lung mechanical properties in the open chest configuration, a partial midsternal thoracotomy was performed and the animals were placed on a rodent mechanical ventilator known under the tradename as "Flexivent", which is sold by Scireq from Montreal, Quebec, Canada.

The ventilator was set at a peak end-expiratory pressure of 3 cmH2O. Initially, respiratory rate and tidal volume were set at 60 cycles/min and 5.1 ml/kg, respectively, during a constant inspiratory flow conventional ventilation. The animals were ventilated on room air for a twenty minute acclimation period and baseline measurements were taken.

In order to create a condition in the lung similar to that in acute respiratory distress syndrome, the animals were treated as follows. The lungs were depleted of surfactant by lavaging. Two aliquots of 10 ml warm saline were injected into the trachea and then slowly retrieved. This surfactant deficiency results in a significant increase in surface tension and lung elastance which leads to alveolar collapse.

Next, the animals were ventilated with conventional ventilation, variable tidal volume ventilation as described in the Lefevre, et al. study and variable peak pressure ventilation in accordance with one embodiment of the present invention. The methods were alternated at 20 minute intervals. Following each ventilation period, an arterial blood sample was taken for blood gas analysis and lung mechanics were measured using the optimal ventilator waveform technique.

An algorithm was created that programmed the Flexivent ventilator system to vary tidal volume in a sequence that would generate an approximately uniform distribution of peak airway pressure around a given mean value. The corresponding distribution of tidal volumes necessary to produce the prescribed distribution of peak airway pressures was generated using Eq. 1. A pressure-volume curve was generated assuming n=12. Next, a sequence of random numbers containing 1800 points was generated by pooling the numbers from a zero mean, uniform distribution between −1 and 1. The sequence was scaled down to have a given standard deviation and added to the mean peak inspiratory pressure which was chosen to be at the knee of the pressure-volume curve. This pressure sequence was then passed through equation 1 which resulted in a sequence of corresponding tidal volume values.

Figure 3:
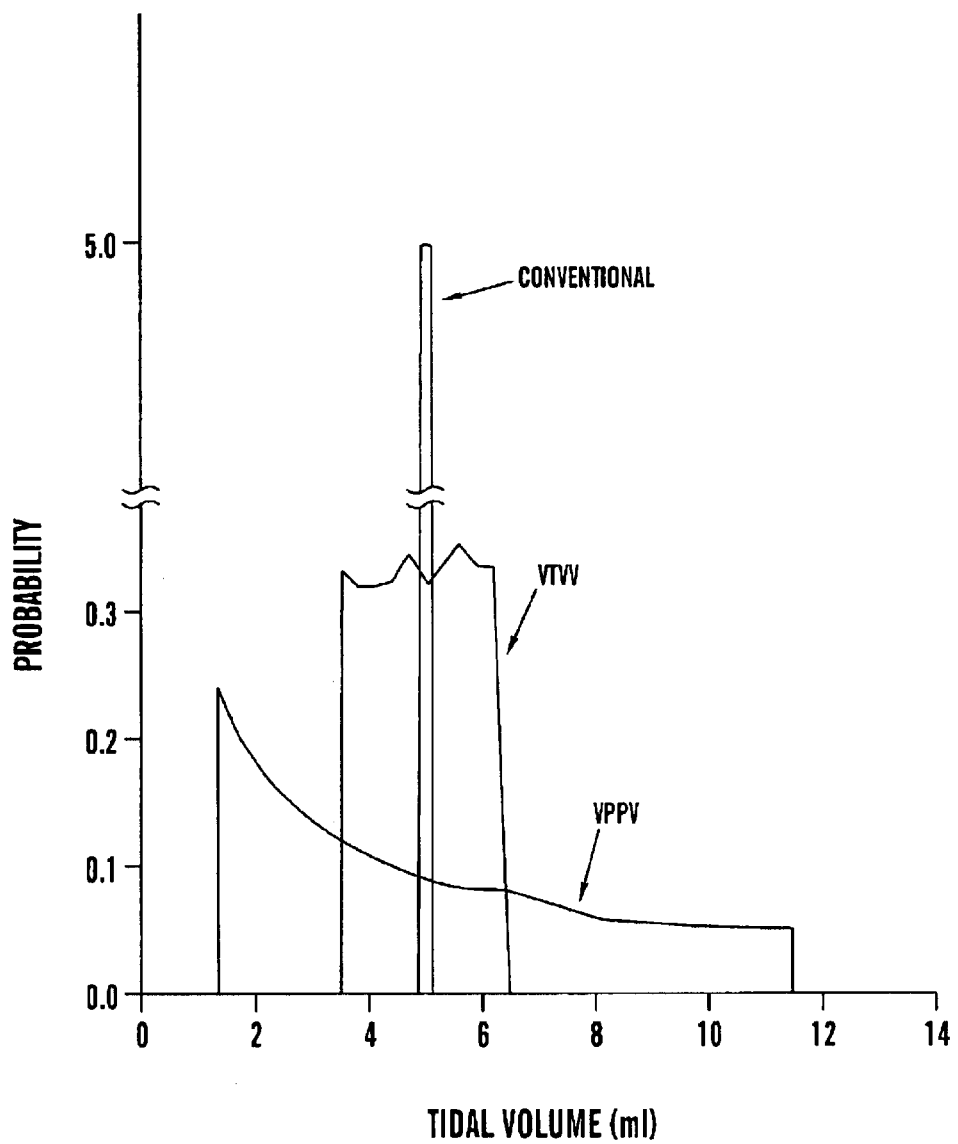
FIG. 3 is a graph of the probability distributions of tidal volumes versus tidal volume of three methods of lung ventilation.

FIG. 3 is a graph that compares the probability density distributions for delivered tidal volumes when using conventional ventilation (CV), variable tidal volume ventilation (VTVV), and variable peak pressure ventilation (VPPV). The tidal volume distribution for conventional ventilation is a spike at the nominated tidal volume. The distribution for the variable tidal volume ventilation is uniform having the same mean as the conventional ventilation. For variable peak pressure ventilation, the distribution is skewed toward lower values, with a finite but smaller probability of delivering larger tidal volumes too. The mean of this distribution is also the same as that of the conventional ventilation.

These tidal volume values were then used to program the ventilator from breath to breath and the corresponding peak airway pressures were measured. The standard deviations for the distributions were chosen to be 10% or 20% of the mean tidal volume for the variable tidal volume ventilation. The standard deviation values for the variable peak pressure ventilation were specified in terms of the normalized pressure and then by converting the pressure sequence to tidal volume sequence as described above.

The inventors discovered that standard deviation values of 0.05 and 0.075 on the normalized pressure scale provided similar variabilities as the 10% and 20% standard deviation values, respectively, for the variable tidal volume ventilation. Finally, to achieve the same minute ventilation, the frequencies were adjusted so that the minute ventilation of the three ventilation modes were equal independent of the standard deviation chosen.

Impedance measurements were also obtained by the inventors of the present invention. The Optimal Ventilator Waveform technique (K. R. Lutchen, K. Yang, D. W. Kaczka and B. Suki; *Optimal ventilator waveforms for estimating low-frequency respiratory impedance in healthy and diseased subjects*, J. Appl. Physiol. 75:478–488, (1993)) is a forced oscillation method that consists of six sine waves with frequencies between 0.5 and 14.25 Hz that are selected according to a non-sum-non-difference criterion which minimizes the nonlinear interaction at the six input frequencies. (B. Suki and K. R. Lutchen, *Pseudorandom signals to estimate apparent transfer and coherence functions of non-linear systems: applications to respiratory mechanics*, IEEE Trans. Biomed. Eng. Vol. 39, November issue, No. 11: 1142–1151, (1992)). The phase angles and amplitudes were optimized so that the input volume waveform has a tidal-like shape. This allowed the measurement of a smooth estimate of lung impedance over a range of frequencies with minimal disruption to mechanical ventilation.

Figure 4:
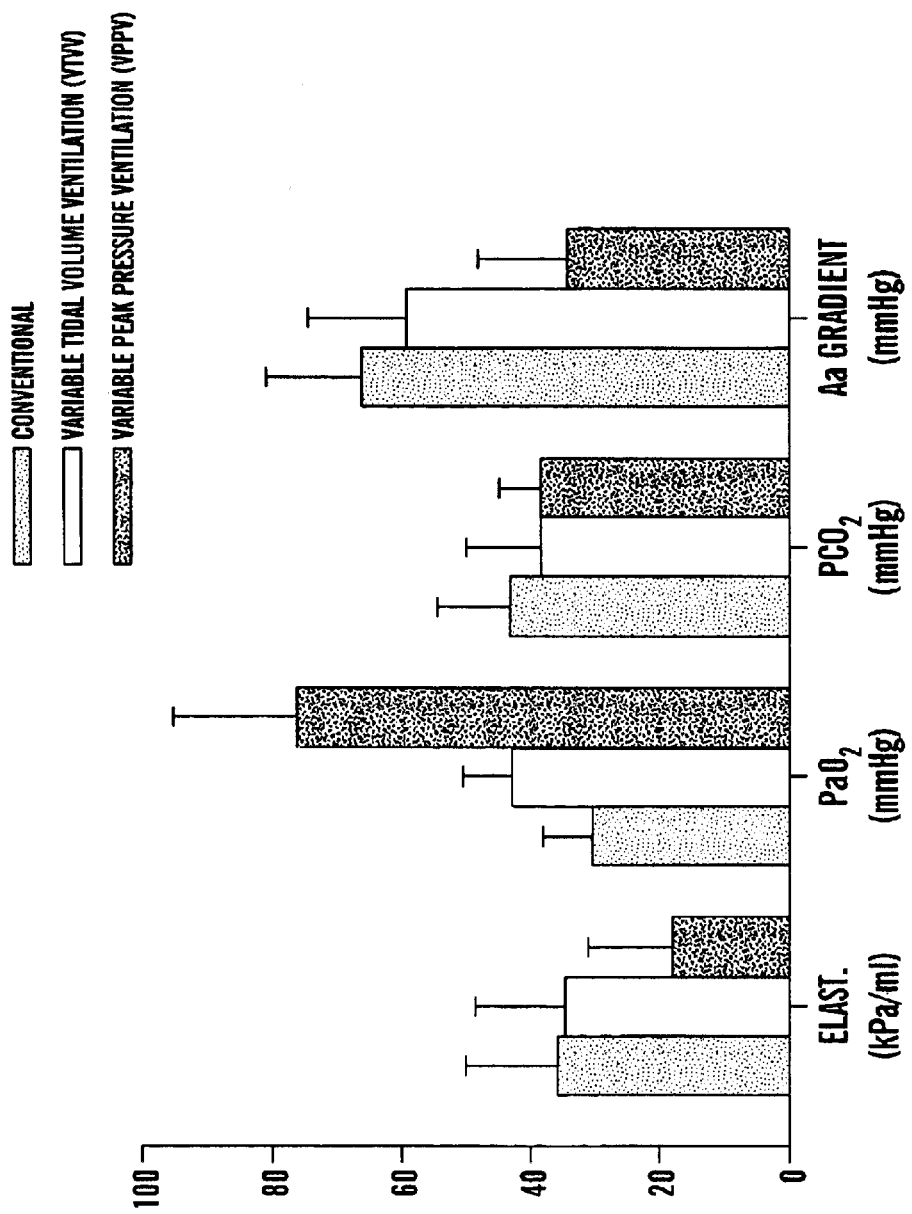
FIG. 4 is a bar chart comparing two conventional modes of ventilation with one exemplary embodiment of the ventilation system and method of the present invention.

FIG. 4 is a bar chart comparing lung elastance as a measure of collapse, arterial oxygen pressure, carbon dioxide pressure and alveolar to arterial pressure gradient as a measure of gas exchange using the three methods of ventilation. The three methods being the conventional ventilation on the left, the variable tidal volume ventilation mode as described by Lefevre et al. in the middle and the variable peak pressure ventilation mode in accordance with one embodiment of the present invention. FIG. 4 shows that lung elastance is much lower showing less collapse; the arterial oxygen is about twice as high; the carbon dioxide pressure is slightly lower and the alveolar to arterial pressure gradient is much improved when using an embodiment of the present invention. Thus, these results show that variable peak pressure ventilation in accordance with the present invention is superior to any prior ventilation mode.

Figure 5:
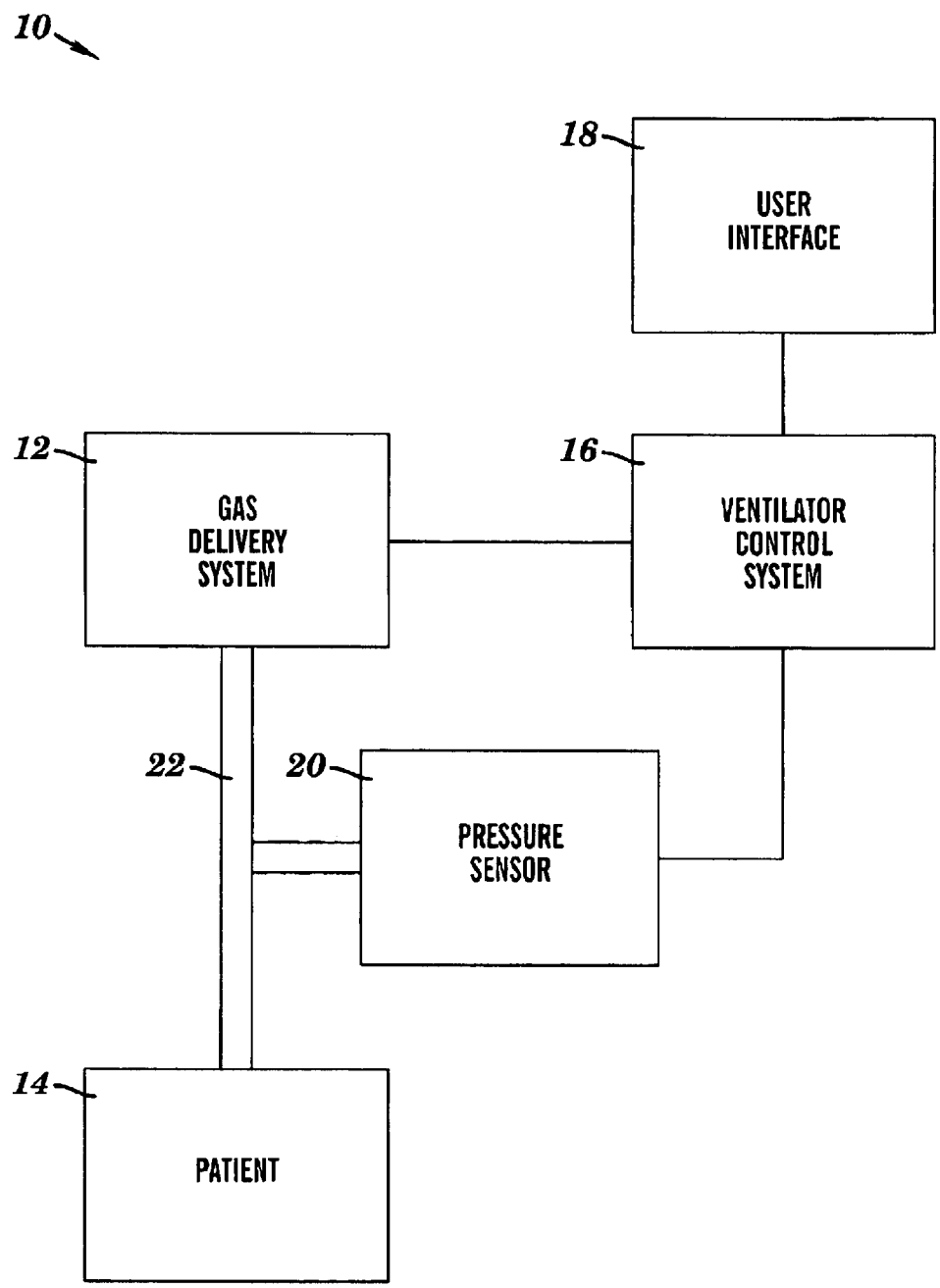
FIG. 5 is a schematic block diagram of an exemplary embodiment of a ventilator system in accordance with the present invention.

FIG. 5 is a schematic diagram of one exemplary embodiment of a ventilator system in accordance with the present invention. The ventilator system 10 includes a gas delivery system 12 that is in communication with a patient or other living being 14. The gas delivery system 12 may be a conventional mechanical ventilating system or the like. The ventilator system 10 includes a ventilator control system 16 that is in communication with the gas delivery system 12. The ventilator control system 16 may include a processor (not shown) that is programmed to control the gas delivery system 12 such that the gas delivery system 12 delivers sequential breaths of gas as has been described above.

The ventilator control system 16 may optionally be in communication with a user interface 18 and a pressure sensor 20 or other feedback device such as an air flow meter or the like. The optional user interface 18 may be adapted to enable a user to provide the ventilator control system 16 with information that, in turn, enables the ventilator control system 16 to operate the gas delivery system in accordance with the present invention. For example, the user interface 18 may include a keyboard, mouse or the like that enables a user to enter weight, optionally age information and also an initial estimate of the degree of severity of lung damage in the patient 14 by providing an initial value for n. The user may also provide an initial estimate of the pressure-volume curve for the lung of the patient. For small animals, the inventors have discovered that the standard deviation may initially be set to 30–40% of the knee pressure. The user interface 18 may also include an interactive display or the like to present information to a user so that a user may be able to adjust the mean volume of air being delivered to the patient as well as subsequent values for n.

The pressure sensor 20 is in communication with a gas line 22 that enables the gas delivery system 12 to communicate with the patient 14. The pressure sensor 20 is adapted to sense the pressure of the gas in the gas line 22 and to supply a signal that indicates the pressure to the ventilator control system 16. Preferably, the pressure sensor 20 has a pressure tap (not shown) that is as close to the patient as possible. By monitoring the pressures being sensed by the pressure sensor 20 and knowing the corresponding volumes of gas being delivered by the gas delivery system 12, the ventilator control system 16 may determine the pressure-volume characteristics of the lungs of the patient 14. These characteristics may then be used to fine tune or adjust the control parameters of the ventilator system 10. For example, a user may observe on the user interface 18 that the pressure-volume characteristics of the lungs of the patient 14 may not be as severe as a current value of n would indicate. In such a case, a user may interact with the user interface 18 and reduce the value of n. In this manner, as the condition of the lung of the patient 14 improves a user may then be able to reduce the value of n and wean the patient off of the ventilator more quickly than has previously been realized. Alternatively, the control system 16 may be programmed to automatically and periodically update the pressure-volume curve, revise the associated lung characteristics and adapt the pressure/volume sequences being delivered.

While this invention has been described in connection with the specific embodiments outlined above, it is evident that many alternatives, modifications and variations are apparent to those skilled in the art. Accordingly, the preferred embodiments of the invention as set forth above are intended to be illustrative and not limiting. Various changes may be made without departing from the spirit and scope of the invention.

What is claimed is:

1. A method for ventilating a lung in a living being, said method comprising the steps of:
providing a first volume of gas to said living being; and providing a second volume of gas to said living being, wherein the second volume of gas provided, V, is determined by the following equation, is $V=P^n$, wherein P is the normalized pressure of the gas, and the lung comprises a variable number, n, of generations of collapsed airways, and wherein each of said volumes of gas being provided has a volume that is based upon a corresponding predetermined peak inspiratory pressure.

2. The method of claim 1, wherein each of said corresponding predetermined peak pressures is based upon a predetermined distribution of peak pressures about a predetermined mean peak inspiratory pressure.

3. The method of claim 2, wherein said predetermined mean peak inspiratory pressure is based upon a knee in the pressure-volume characteristics of said lung.

4. The method of claim 2, wherein said distribution is a Gaussian distribution.

5. The method of claim 2, wherein said distribution is symmetric about the predetermined peak inspiratory pressure.

6. The method of claim 1, wherein the relationship between said volume of gas and said corresponding predetermined peak inspiratory pressure is a power law relationship.

7. The method of claim 6, wherein said power law relationship has a predetermined exponent.

8. The method of claim 7, wherein said exponent is based upon the number of generations of collapsed airways in said lung.

9. The method of claim 7, wherein said exponent is based upon an approximation of the number of collapsed airways in said lung.

10. The method of claim 6, wherein said relationship is further based upon the elasticity of open airways in said lung.

11. The method of claim 1, further comprising the steps of: measuring the peak inspiratory pressure of each of said first and second volumes of gas; providing a third volume of gas based upon a revised predetermined peak inspiratory pressure.

12. The method of claim 11, wherein said step of measuring the peak inspiratory pressure comprises measuring the peak inspiratory pressure adjacent a mouth of said living being.

13. A ventilator for a lung in a living being, said ventilator comprising: a gas delivery system adapted to provide a volume of gas to a lung in a living being, wherein the second volume of gas provided, V, is determined by the formula $V=P^n$, wherein the lung comprises a variable number, n, of generations of collapsed airways and P is the normalized pressure of the gas; and a processor that is programmed to control gas entry in the following manner, wherein the volume of gas, V, to be provided to a lung in a living being is determined by the formula $V=P^n$, wherein the lung comprises a variable number, n, of generations of collapsed airways and P is the normalized pressure of the gas such that a first volume of gas is delivered to said lung and a second volume of gas to said lung wherein, each of said volumes of gas delivered is determined by said processor based upon said program.

14. The ventilator of claim 13, wherein each of said corresponding predetermined peak pressures is based upon a predetermined distribution of peak pressures about a predetermined mean peak inspiratory pressure.

15. The ventilator of claim 14, wherein said predetermined mean peak inspiratory pressure is based upon a knee in the pressure-volume characteristics of said lung.

16. The ventilator of claim 14, wherein said distribution is a Gaussian distribution.

17. The ventilator of claim 14, wherein said distribution is symmetric about the predetermined peak inspiratory pressure.

18. The ventilator of claim 13, wherein the relationship between said volume of gas and said corresponding predetermined peak inspiratory pressure is a power law relationship.

19. The ventilator of claim 18, wherein said power law relationship has a predetermined exponent.

20. The ventilator of claim 19, wherein said exponent is based upon the number of generations of collapsed airways in said lung.

21. The ventilator of claim 19, wherein said exponent is based upon an approximation of the number of collapsed airways in said lung.

22. The ventilator of claim 18, wherein said relationship is further based upon elasticity of open airways in said lung.

23. The ventilator of claim 13, further comprising a pressure sensor in communication with said lung and wherein said processor is adapted to control said gas delivery system to provide a third volume of gas based upon a revised predetermined peak inspiratory pressure.

24. The ventilator of claim 23, wherein said pressure sensor is adjacent a mouth of said living being.

* * * * *